United States Patent [19]

Schlossmann et al.

[11] Patent Number: 4,976,964

[45] Date of Patent: Dec. 11, 1990

[54] MEDICAMENT FORMULATION CONTAINING DIHYDROPYRIDINES AND A PROCESS FOR ITS PREPARATION

[75] Inventors: Klaus Schlossmann, Wuppertal; Alfred Zembrod, Bergisch-Gladbach; Stanislav Kazda, Wuppertal; Peter Serno, Cologne; Bernd Klinksiek, Bergisch-Gladbach, all of Fed. Rep. of Germany

[73] Assignee: Bayer Aktiengesellschaft, Leverkusen, Fed. Rep. of Germany

[21] Appl. No.: 852,584

[22] Filed: Apr. 16, 1986

[30] Foreign Application Priority Data

Apr. 27, 1985 [DE] Fed. Rep. of Germany ....... 3515335

[51] Int. Cl.$^5$ ..................... A61K 37/22; A61K 25/26; B32B 5/16; B01J 13/02
[52] U.S. Cl. ..................... 424/450; 264/4.1; 264/4.3; 264/4.6; 428/402.2; 424/417
[58] Field of Search .............................. 424/450, 417; 428/402.2; 264/4.1, 4.3, 4.6

[56] References Cited

FOREIGN PATENT DOCUMENTS 0102324 3/1984 European Pat. Off. .
0143305 6/1985 European Pat. Off. .
1792410 11/1971 Fed. Rep. of Germany .
2822882 12/1978 Fed. Rep. of Germany .
3339861 5/1985 Fed. Rep. of Germany .
0012127 1/1985 Japan ..................................... 264/4.1
1173862 12/1969 United Kingdom .

OTHER PUBLICATIONS

Chemical Abstracts, Band 91, 1979, Columbus, Ohio, USA, Y. Matsuno et al., "Lolubilizotion of nifedipine" Seite 350, Spalte 1, Zusammenfassung-Nr. 163 057s & Jpn. Kokai Tokkyo Koho, 79–55 714, Ota Pharmaceutical Co. Ltd.; Tokai Capsule Co., Ltd.
Chemical Abstracts 102: 2255k (1–7–85).

*Primary Examiner*—Douglas W. Robinson
*Attorney, Agent, or Firm*—Sprung Horn Kramer & Woods

[57] ABSTRACT

In the parenteral administration of a dihydropyridine, the improvement which comprises administering the dihydropyridine in an aqueous medium of pH 3 to 8.5 having dispersed therein liposomes with an average diameter of 20–1000 nm, the liposome membrane containng the following constituents by weight:

(a) a part of a dihydropyridine, and
(b) 5–500 parts of lipids.

The aqueous medium is storage stable and readily injectable.

15 Claims, No Drawings

MEDICAMENT FORMULATION CONTAINING DIHYDROPYRIDINES AND A PROCESS FOR ITS PREPARATION

The invention relates to a medicament formulation which can be administered parenterally and contains dihydropyridines in a matrix of liposomes, and to a process for its preparation.

It is known that dihydropyridines have very powerful actions which influence the circulation and are therefore suitable, for example, for combating high blood pressure, heart diseases and ischaemic cerebral diseases (compare British Pat. No. 1,173,862).

Because of their photosensitivity and their poor solubility, a number of difficulties arise in the pharmaceutical formulation of medicament formulations based on dihydropyridines.

All previous attempts to compensate for the poor solubility, for example of nimodipine, by certain measures and at the same time to guarantee a good bioavailability have a number of disadvantages. The use of surface-active substances, solubilizing agents and certain excipients which have a particular surface frequently leads to administration forms in which the products are undesirably large. To facilitate swallowing, such tablets or capsules are frequently converted into specific forms, such as, for example, ellipsoids or longitudinal shapes, but this also no longer gives satisfactory results in products weighing more than 400 mg. More frequent taking of smaller products is also not a satisfactory solution.

To combat some diseases, for example ischaemic cerebral diseases, it is desirable to administer the dihydropyridines parenterally (intravenously or intraarterially) in a solution.

Since, as described, the dihydropyridines have a poor solubility in water, an injectable formulation has previously first had to be formulated with the aid of organic solvents for parenteral administration.

As is known, the use of organic solvents is not without objection from the clinical-therapeutic viewpoint. Thus, for example, tissue damage and local irritation effects in the vessels may arise.

Such side effects on parenteral administration of dihydropyridines restrict the use of organic solvents.

It has now been found that the dihydropyridine compounds can be administered without the addition of organic solvents if they are incorporated in the matrix of liposomes.

The invention thus elates to a medicament formulation which can be administered parenterally and contains liposomes with an average diameter of 20-1000 nm, preferably 50-200 nm, the liposome membrane ccntaining the following constituents:

(a) 1 part by weight of a dihydropyridine; and
(b) 5-500 parts by weight, preferably 20-200 parts by weight, of lipids, and these liposomes being dispersed in an aqueous medium with a pH value of 3.0 to 8.5.

The dihydropyridines are dispersed in the membrane of the liposomes.

By liposomes there are understood artificially prepared vesicles, the membrane material of which chiefly consists of naturally occurring membrane components, such as phospholipids. If a compound is lipid-soluble, like the dihydropyridine derivatives, it can be incorporated in the lipid membrane, in contrast to water-soluble substances, which are enclosed in the aqueous inner volume of the vesicles on preparation of the liposomes.

Preferred dihydropyridines which may be mentioned are compounds of the formula I

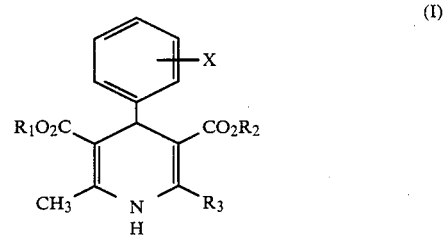

(I)

in which $R_1$ denotes $C_1$–$C_4$-alkyl, optionally substituted by $C_1$–$C_3$-alkoxy, $R_2$ denotes $C_1$–$C_{10}$-alkyl, optionally substituted by $C_1$–$C_3$-alkoxy, trifluoromethyl, N-methyl-N-benzylamino or benzyl, $R_3$ denotes $C_1$–$C_4$-alkyl, cyano or hydroxymethyl and X denotes 2- or 3-nitro, 2,3-dichloro, a 2,3-ring member consisting of =N—O—N= or 2- or 3-trifluoromethyl.

The compounds of the following table may be mentioned as particularly preferred:

TABLE 1

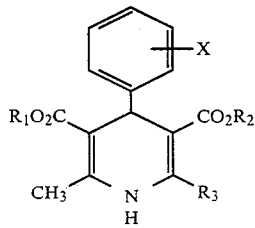

| No. | X | $R^1$ | $R^2$ | $R^3$ | Generic |
|---|---|---|---|---|---|
| 1 | 2-$NO_2$ | $CH_3$ | $CH_3$ | $CH_3$ | Nifedipine |
| 2 | 3-$NO_2$ | $nPrOCH_2CH_2$ | $nPrOCH_2CH_2$ | $CH_3$ | Niludipine |
| 3 | 3-$NO_2$ | $C_2H_5$ | $CH_3$ | $CH_3$ | Nitrendipine |
| 4 | 2-$NO_2$ | $CH_3$ | $(CH_3)_2CHCH_2$ | $CH_3$ | Nisoldipine |
| 5 | 3-$NO_2$ | $CH(CH_3)_2$ | $(CH_2)_2$—O—$CH_3$ | $CH_3$ | Nimodipine |
| 6 | 3-$NO_2$ | $C_2H_5$ | $C_{10}H_{21}(n)$ | $CH_3$ | |
| 7 | 2-Cl | $CH_3$ | $CH_2$—$CF_3$ | $CH_3$ | |
| 8 | 2-Cl | $C_2H_5$ | $CH_2$—$CF_3$ | $CH_3$ | |

TABLE 1-continued

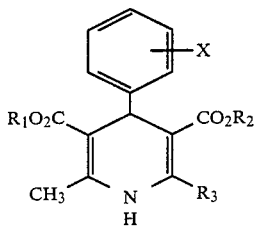

| No. | X | R¹ | R² | R³ | Generic |
|---|---|---|---|---|---|
| 9 | 3-$NO_2$ | $CH(CH_3)_2$ | n-PrO—$CH_2CH_2$ | $CH_3$ | |
| 10 | 3-$NO_2$ | $CH_3$ | $C_6H_5CH_2N(CH_3)CH_2CH_2$ | $CH_3$ | Nicardipine |
| 11 | 2,3-$Cl_2$ | $C_2H_5$ | $CH_3$ | $CH_3$ | Felodipine |
| 12 | 2,3=C—O—N= | $C_2H_5$ | $C_2H_5$ | $CH_3$ | |
| 13 | 2,3=N—O—N= | $CH_3$ | $CH(CH_3)_2$ | $CH_3$ | |
| 14 | 3-$NO_2$ | $C_2H_5$ | $C_2H_5$ | $CH_2OH$ | |
| 15 | 3-$NO_2$ | $CH_3$ | $CH_3$ | CN | | n-Pr = n-Propyl

Compounds which may be mentioned particular are: nifedipine, nimodipine, nitrencipine and nisoldipine.

Possible lipids for the liposome membrane are: phosphatidylcholine (lecithin), phosphatidylserine, phosphatidylethanolamine, phosphatidylglycerol, phosphatidylinositol, sphingomyelin and cholesterol.

The aqueous medium preferably has a pH value of 7.0 to 7.5. It can contain customary auxiliaries and additives, such as, for example, physiological saline solution or other isotonic salt solutions.

The solution can moreover contain the customary pharmaceutically acceptable buffers, such as phosphate buffer, for the purpose of establishing the pH.

The weight ratio of lipids (which form the liposomes in water) to water is preferably 20 to 100 parts by weight of water per part by weight of lipid.

On prolonged storage of the medicament formulation according to the invention and at low temperature, the dihydropyridines may leave the liposome membrane under certain circumstances and crystallize out in the aqueous external medium.

In order substantially to prevent the phenomenon, up to 20% by weight, preferably up to 10% by weight, of a polyalcohol, based on the aqueous solution, may be added.

Preferred polyalcohols which may be mentioned are those which contain 2-6 C atoms and 2-6 hydroxyl groups, and mono-, oligo- and polysaccharides.

Polyalcohols which may be mentioned as particularly preferred are: dihydroxypropane, glycerol, mannitol, glucose, sucrose and dextran.

The medicament formulation according to the invention can thus be frozen without problems.

The storage life is considerably increased in this manner.

The invention also relates to a process for the preparation of the medicament formulations, which is characterized in that 1 part by weight of the dihydropyridine and 5-500 parts by weight of lipid are dissolved in organic solvents, the solvent is then removed and, after addition of an aqueous medium with a pH value of 6.5 to 8, the residue is dispersed at temperatures between 20° and 80° C.

Examples of possible organic solvents are: methanol, ethanol, acetone and highly volatile halogenohydrocarbons.

The dispersion is prepared using known methods, preferably by means of ultra-sound, by means of high-speed stirrers or by means of a high-pressure homogenizer. The dispersion can be sterilized by heat, after its preparation. It is also possible to convert it into a dry powder by freeze-drying. The powder thus dried can then be redispersed again, as required, by means of aqueous solutions of pH 3.0-8.5.

The invention may be illustrated with the aid of the following examples:

EXAMPLE 1

Nimodipine liposomes are prepared with a load concentration of 0.3 mg/ml or 1 mg/ml by ultrasonic treatment. For 10 ml batches, 3 or 10 mg of nimodipine and 200 mg of soy bean lecithin are dissolved in about 0.2 ml of methanol/2ml of chloroform. The solvent is evaporated off until a solid, dry film remains. After addition of 10 ml of 0.02 M Na-phosphate buffer (pH 7.3), the solid is dispersed with an immersion ultrasonic apparatus (Branson B 12 with standard ½ inch finger) for 8 minutes at about 55° C. under a blanket gas of argon. The dispersion is then centrifuged at 1200 g for 10 minutes to remove the titanium articles abraded off from the ultrasonic finger. All the preparations are carried out under Na light because of the photosensitivity of nimodipine. The dynamic light scattering method is suitable for determining the average particle size of he liposomes. The nimodipine liposomes have an average diameter in the range from 50 to 100 nm.

EXAMPLE 2

In each case 3 or 10 mg of nimodipine and 200 mg of soy bean lecithin are dissolved in 0.2 ml of methanol/2 ml of chloroform. The solvent is evaporated off until a solid dry film remains. Before the dispersion, 10% by weight of mannitol is added to the aqueous medium required for the preparation of the liposomes in order to stabilize the nimodipine load on the liposomes. Further preparation, working up and analytical determination of the parameters of the liposomes are carried out as in Example 1.

EXAMPLE 3

As Example 2. However, before the dispersion, 5.2% by weight of glycerol is added to the aqueous medium for stabilization of the nimodipine load on the liposomes. The liposomes prepared with added glycerol are frozen slowly in a freezing cabinet at −20° C. After the dispersions have thawed, the liposome preparations look the same as before freezing. Measurements with the aid of dynamic light scattering showed the same average liposome particle sizes as before freezing.

EXAMPLE 4

20 mg of nimodipine and 2 g of soy bean lecithin are dissolved in 2 ml of methanol/20 ml of chloroform. The solvent is evaporated off. The residue of solid is added, as a powder, to a volume of 100 ml of aqueous Na phosphate buffer (20 mM) containing 4% of propanediol. The solid is dispersed with a high-speed stirrer for about 60 minutes. A nimodipine-containing liposome suspension is formed.

EXAMPLE 5

Phosphatidylserine (2 mg) is added, as a negative charge carrier, to the phosphatidylcholine (lecithin) (200 mg). The further preparation operation is carried out as described in Example 1.

EXAMPLE 6

Instead of 200 mg of soy bean lecithin, a mixture of 200 mg of sphingomyelin plus 2 mg of phosphatidylserine is used as the phospholipid. Further preparation is carried out as in Example 1. The average diameter measured for the liposomes is 58 nm.

EXAMPLE 7

Dipalmitoylphosphatidylcholine (200 mg) and phosphatidylserine (2 mg) are used as phospholipids. Further working up is carried out as in Example 1. The average diameter of the liposomes is 51 nm.

EXAMPLE 8

A chloroform solution of 100 mg of egg lecithin, 8 mg of dicetyl phosphate and 5 mg of nifedipine is evaporated, while gassing with argon. After addition of 10 ml of 0.1 M Na phosphate buffer, pH 7.3, the mixture is subjected to ultrasonic treatment at 40°–45°C. under Na light for 10 minutes.

EXAMPLES 9–11

3 mg of the dihydropyridine compound (see Table 2) and 200 mg of soy bean lecithin are dissolved in 0.2 ml of methanol/2 ml of chloroform. The solvent is evaporated off, while gassing with argon. After addition of 0.02M phosphate buffer, pH 7.3, containing 5.2% of glycerol, the solid is dispered by ultrasonic treatment at 55° C. under argon. The dispersions are centrifuged at 1200 g for 10 minutes. Because of the photosensitivity of the dihydropyridine derivatives, all the preparations are carried out under sodium light. The average particle size of the liposomes is determined by the dynamic light scattering method. The average diameter measured for the liposomes, which are loaded with the dihydropyridine derivatives listed as examples in Table 2, is shown in the Table.

TABLE 2

Average particle size and diameter distribution range of the DHP-loaded liposomes.

| Example | Formula | d [nm] | K2 |
|---|---|---|---|
| 9 | (dihydropyridine structure: H₃COOC, COOCH₃, H₃C, CH₃, NO₂, NH) | 57 | 0.28 |
| 10 | (dihydropyridine structure: H₅C₂OOC, COOCH₃, H₃C, CH₃, NO₂, NH) | 74 | 0.45 |
| 11 | (dihydropyridine structure: CH₃-CH(CH₃)-CH₂OOC, COOCH₃, H₃C, CH₃, NO₂, NH) | 81 | 0.42 |

DHP = dihydropyridine derivative
d = average particle size of the liposomes
K2 = diameter distribution range

EXAMPLE 12

28 mg of nimodipine (see Table 1) and 2.1 g of egg lecithin are dissolved in 5 ml methanol/5 ml chloroform. The solvent is evaporated off, while gassing with argon. After addition of 70 ml of 0.02M phosphate buffer, pH 7.3, containing 8% of trehalose, the solid is dispersed with an immersion ultrasonic apparatus at 55° C., while gassing with argon. After centrifugation of the dispersion at 1200 g for 10 minutes, the nimodipine liposomes have an average diameter of 110 nm.

The dispersion is then divided into 10 ml portions in glass tubes. The glass tubes are firmly closed with special stoppers and sterilized at 120° C. for 20 minutes. As measurements by the dynamic light scattering method have shown, the average particle size is unchanged in comparison with the values before the heat treatment.

EXAMPLE 13

The preparation is carried out as in Example 1, with the difference that the heat treatment is carried out in 2 steps at a temperature of 70° C., in each case for one hour. The tubes are kept at room temperature for 24 hours between the two heating steps at 70° C. The average particle diameter is identical before and after the heat treatment.

EXAMPLE 14

The preparation is carried out as in Example 1, with the difference that the dispersion is lyophilized in a conventional freeze-drying apparatus after the heat treatment. Lyophilization gives a dry powder. If 30 ml of distilled water are added to 1 g of the dry powder which has been kept at room temperature for several weeks, a homogeneous aqueous dispersion is formed in a few minutes by manual shaking. The average particle diameter of this dispersion is unchanged in comparison with the measurement value obtained before the lyophilization (110 nm).

EXAMPLE 15

150 g of egg lecithin and 1 g of nimodipine are dissolved in 200 ml of ethanol. The solvent is evaporated at 50°–60° C. 5 l of an aqueous citrate buffer (pH=6.7) are added to the dry substance thus prepared. The buffer contains 4.7% of D-mannitol. After an incubation time of about 24 hours, the vessel containing the solid and the aqueous phase is shaken thoroughly, a crude dispersion forming. This crude dispersion is further dispersed in a high-pressure homogenizer. The apparatus used (jet disperser) operates under a pressure of 250 bar. It allows circulatory operation (recycling of the discharged material into the inlet channel). After 20 passes, a liposome dispersion with an average particle size of 163 nm is obtained.

EXAMPLE 16

Pharmacological action of nimodipine liposomes

The therapeutic use of the parenteral administration form of nimodipine is based on its dilating action on cerebral vessels. Its action of this type—an increase in the blood supply to the brain—can be demonstrated in animal experiments with the aid of the $^{133}$xenon clearance in the brain.

The washing out (clearance) of intraarterially injected $^{133}$xenon is used as a measure for cerebral circulation on cats which have been anaesthetized with Ketamine®. The radioactively labelled $^{133}$xenon is injected into the artery which leads to the brain and the radioactive emission over the cranium (over the temporooccipital cortex) is recorded with the aid of γ-sensitive pickups. The magnitude of the circulation in the gray cerebral matter is then determined from the clearance curve thus obtained in accordance with the formula $$f = \frac{\lambda \ln 2}{T_{\frac{1}{2}}}.$$

λ=distribution coefficient of xenon
$T_{\frac{1}{2}}$=half life of the initial linear part of the clearance curve.

At the same time, the mean arterial pressure in the aorta femoralis is recorded by means of a Statham pressure pickup.

Nimodipine in the liposome formulation was administered intraarterially, in increasing doses, into the artery leading to the brain. In this form, nimodipine increases cerebral circulation in a dose-dependent manner in a dose range of 0.0001–0.00315 (Table 3).

TABLE 3

Increase in cerebral circulation in cats with nimodipine in liposomes

| Nimodipine mg/kg intraarterially | 0.0001 | 0.0003 | 0.001 | 0.003 |
|---|---|---|---|---|
| Increase in cerebral circulation in % | 18 ± 5.1 | 34 ± 8.1 | 37 ± 7.5 | 57 ± 16.0 |

The maximum increase in cerebral circulation following nimodipine in the liposome formulation was achieved at a dose of 0.003 mg/kg. It was 57 ± 16% in comparison with the starting value.

It will be understood that the specification and examples are illustrative but not limitative of the present invention and that other embodiments within the spirit and scope of the invention will suggest themselves to those skilled in the art.

What is claimed:

1. An aqueous composition of pH 3 to 8.5 having dispersed therein liposomes with an average diameter of 20–1000 nm, the following constituents in the indicated amounts by weight forming the liposome membrane:
   (a) one part by weight of a dihydropyridine of the formula

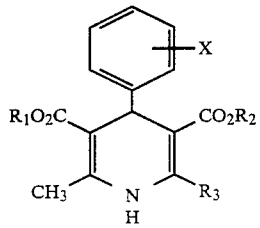

in which
   $R_1$ is $C_1$–$C_4$-alkyl, optionally substituted by $C_1$–$C_3$-alkoxy,
   $R_2$ is $C_1$–$C_{10}$-alkyl, optionally substituted by $C_1$–$C_3$-alkoxy, trifluoromethyl, N-methyl-N-benzyl-amino or benzyl,
   $R_3$ is $C_1$–$C_4$-alkyl, cyano or hydroxymethyl, and X is 2-or 3-nitro, 2,3-dichloro, a 2,3-ring member consisting of =N—O—N= or 2- or 3-trifluoromethyl, and
   (b) 5–500 parts of lipids.

2. A composition according to claim 1, wherein the liposomes have an average diameter of 50–200 nm.

3. A composition according to claim 1, wherein the liposome membrane contains 20–200 parts by weight of lipid.

4. A composition according to claim 1, having a pH of 7 to 7.5.

5. A composition according to claim 1, containing up to 20% by weight of a polyalcohol.

6. A composition according to claim 1, wherein the dihydropyridine comprises nimodipine.

7. A composition according to claim 6, having a pH of 7 to 7.5 and containing up to 20% by weight of a polyalcohol, the liposomes having an average diameter of 50–200 nm and the liposome membrane containing 20–200 parts by weight of lipid.

8. A process for the preparation of an aqueous composition according to claim 1, comprising dissolving the dihydropyridine and lipid in an organic solvent, removing the solvent, adding an aqueous medium with a pH value of 6.5 to 8, and dispersing at a temperature between 20° and 80° C.

9. The process according to claim 8, wherein the solvent is at least one of methanol, ethanol, acetone and a highly volatile halogenohydrocarbon.

10. The process according to claim 8, wherein the dispersing step is effected by means of ultra-sound, a high-speed stirrer or a high-pressure homogenizer.

11. The process according to claim 8, including the further step of sterilizing the liposome dispersion by heating at 120° C. for at least 20 minutes.

12. The process according to claim 8, including the further step of sterilizing the liposome dispersion by heating at 70° C. for at least 1 hour.

13. The process according to claim 12, wherein after about 24 hours the dispersion is again heated at 70° C. for at least 1 hour.

14. A method of producing a storage stable aqueous composition dispersible dry dihydropyridine powder, comprising dissolving a dihydropyridine and 5–500 times its weight of lipids in an organic solvent, removing the solvent, adding an aqueous medium with a pH value of 6.5 to 8, dispersing at a temperature between 20° and 80° C., adding to the dispersion a polyalcohol, and lyophilizing.

15. In the parenteral administration of a dihydropyridine, the improvement which comprises administering the dihydropyridine in an aqueous composition according to claim 1.

* * * * *